United States Patent [19]
Chiesi et al.

[11] Patent Number: 5,855,916
[45] Date of Patent: Jan. 5, 1999

[54] HIGHLY SOLUBLE MULTICOMPONENT INCLUSION COMPLEXES CONTAINING A BASE TYPE DRUG, AN ACID AND A CYCLODEXTRIN

[75] Inventors: Paolo Chiesi; Paolo Ventura; Massimo Pasini; Jösef Szejtli; Maria Vikmon; Enrico Redenti, all of Parma, Italy

[73] Assignee: Chiesi Farmaceutici S.p.A., Parma, Italy

[21] Appl. No.: 418,519

[22] PCT Filed: Jan. 26, 1994

[86] PCT No.: PCT/EP94/00205

§ 371 Date: Nov. 15, 1995

§ 102(e) Date: Nov. 15, 1995

[87] PCT Pub. No.: WO94/16733

PCT Pub. Date: Aug. 4, 1994

[30] Foreign Application Priority Data

Jan. 29, 1993 [IT] Italy .................................. MI93A0141

[51] Int. Cl.⁶ .............................. A61K 9/10; A61K 47/40
[52] U.S. Cl. ............................................. 424/488; 514/777
[58] Field of Search ..................................... 424/484, 488; 514/777

[56] References Cited

U.S. PATENT DOCUMENTS 4,365,061 12/1982 Szejtli et al. .
5,646,131 7/1997 Badwan et al. .

*Primary Examiner*—Edward J. Webman
*Attorney, Agent, or Firm*—Oblon, Spivak, McClelland, Maier & Neustadt, P. C.

[57] ABSTRACT

A multicomponent inclusion complex of a basic drug, an acid and a cyclodextrin has enhanced water-solubility.

19 Claims, No Drawings

HIGHLY SOLUBLE MULTICOMPONENT INCLUSION COMPLEXES CONTAINING A BASE TYPE DRUG, AN ACID AND A CYCLODEXTRIN

BACKGROUND OF THE INVENTION

1. Field of the Invention

The invention relates to highly soluble multicomponent inclusion complexes consisting of a basic-type drug, a cyclodextrin and an acid.

2. Discussion of the Background

The term basic-type drug refers to organic compounds bearing hydrophobic groups and nitrogen basic groups, such as amino, amine and guanidino groups.

A lot of drugs bear aliphatic or aromatic amine groups. These types of drugs usually have very low aqueous solubility in base form which often hampers their application.

Salt formation with inorganic or organic acids is a common method, which is very often used to increase the solubility of base-type drugs. However sometimes even the salts are poorly soluble, or by other reasons a conventional salt formation is inadequate.

It is known that the aqueous solubility of base-type drugs or their salts is much higher at low pH values whereas it is very poor at higher pH of the intestinal tract, comprised between pH 5–8. Therefore, the release site from formulations of such drugs is restricted to the stomach or to the upper part of the intestinal tract and such properties make impossible the preparation and use of such drugs in controlled release formulation, wherever it is necessary to ensure the dissolution of the drug in the intestinal juice.

The difficulties originated from the low aqueous solubility of certain drugs, such as low rate and percent of dissolution from pharmaceutical formulations, together with poor and/or variable bioavailability can be overcome by cyclodextrin complexation.

In prior art a lot of amine type drugs, such as terfenadine and cinnarizine, have been successfully complexed with cyclodextrins, with good results. However, low aqueous solubility of β-cyclodextrin hinders its applications as complexing agent from a technological point of view.

Soluble complexes can be prepared from homogeneous drug-cyclodextrin solutions by removing water by freeze-drying or spray drying. This technique is widely used in the prior art in case of using well soluble β-cyclodextrin derivatives such as methyl or hydroxypropyl β-cyclodextrins.

The solubilizing capacity of β-cyclodextrin is strongly limited by its low aqueous solubility. Therefore large volume of solutions have to be used for the preparation of soluble complexes.

SUMMARY OF THE INVENTION

Surprisingly, it has now been found that the presence of acids in the formation of complexes of amine type drugs with cyclodextrins results in easily water soluble complexes with extremely high concentrations both of the guest molecule and of cyclodextrin.

Even more surprisingly it has been found that, when the cyclodextrin is β-cyclodextrin, the presence of an acid considerably enhances its water solubility.

In fact, in this kind of complexes, not only the solubility of the hydrophobic guest results enhanced by several orders of magnitude, but also the solubility of the hydrophilic β-cyclodextrin may be increased up to more than 10 times.

Up to now, a mutual host-guest solubility enhancement up to a very modest extent has been reported only in the case of fendiline hydrochloride-β-CD (Stadler Szöke A. et al. . . , J. Inclusion Phenomena 3, 71–84, 1985).

A first aspect of the present invention therefore relates to multicomponent inclusion complexes fundamentally consisting of a base type drug, a cyclodextrin and an acid.

A second aspect of the present invention relates to the use of an acid in the preparation of complexes with a cyclodextrin, and particularly with β-cyclodextrin, with the purpose of increasing water solubility of the cyclodextrin itself.

The solubility increase of the guest molecule and/or the cyclodextrin may occur both in the presence of inorganic acids and of organic acids.

Examples of inorganic acids are halogenhydric acids, such as hydrochloric, hydrobromic acid.

Examples of organic acids are aliphatic carboxylic acids, such as acetic acid, propionic acid, butyric acid, oxalic acid, succinic acid, glutaric acid, pimelic acid, tartaric acid, malic acid, citric acid, maleic acid, malonic acid. Particularly favourable results have been obtained with aliphatic carboxylic acids bearing one or more oxygenated substituents in the aliphatic chain, preferably keto groups or hydroxy groups. The most evident solubilizing effects have been obtained with organic acids, and among them, the best results have been achieved with aliphatic carboxylic acids bearing one or more oxygenated substituents in the aliphatic chain, such as citric acid, tartaric acid, α-ketoglutaric acid, threonic acid.

In prior art the application of organic acids to drug complexes with cyclodextrins are very limited and concern:

a) the improvement of chemical stability of carmoful (1-hexylcarbamoyl-5-fluorouracil, HCFU) in β-cyclodextrin complexes prepared by the kneading method with an organic acid, such as L(+)-tartaric, DL-malic, citric, maleic, malonic acid.

The organic acids can provide an acidic environment around the complex after water elimination, since HCFU is chemically stable under acidic conditions (Japanese Patent Application N* 60185772, by Mitsui; Chem Abs 104:155972 and Kikuchi M et al. Chem Pharm Bull 35(1), 315–319, 1987);

b) the use of a solid organic acid (selected from citric, tartaric or malic acid) in solid pharmaceutical compositions containing cephalosporins and a cyclodextrin in order to improve their dissolution and bioavailability with respect to compositions containing crystalline cellulose instead of a α-cyclodextrin (European Patent EP 163433, by Takeda; Chem Abs 105:12098n), c) the simultaneous administration of citric acid and cinnarizine or its complex with β-cyclodextrin to evaluate its bioavailability: however, no significant difference has been found between the two administration forms (Tokumura T et al. J. Incl. Phenom 2, 511–521, 1984 and Chem Pharm Bull 33(7), 2962–2967, 1988).

Up to now neither multicomponent inclusion complexes containing a cyclodextrin, a base type active ingredient and an acid have been described, nor a so high improvement of solubility of an active ingredient by complexation with a cyclodextrin has been obtained.

The simultaneous large solubility enhancement for β-CD at least up to the here disclosed extent is also a new and surprising observation.

A further object of the present invention is a general method for the preparation of base-type drug:βCD:acid complex consisting in the removal of water from the highly supersaturated solution of the components in distilled water. According to the present invention said process comprises the following steps:

a) suspension in distilled water of suitable quantities of drug, cyclodextrin and acid;
b) homogenization of the suspension obtained in step a) by stirring and/or sonication to obtain a clear or slightly opalescent solution;
c) filtration of the solution obtained in step b) by using a suitable system to obtain a clear solution;
d) dehydration of the solution obtained in step c) by using usual dehydration methods such as freeze-drying, spray-drying, stove-drying or similar.

The same method can be used in order to prepare complexes with α-CD, γ CD, hydroxypropyl-βCD, dimethyl-βCD, RAMEB (RAndom MEthylated (β-CD) or other cyclodextrin derivatives. Even more supersaturated solutions with improved storage stability, which can be used to prepare liquid pharmaceutical compositions for oral or parenteral administration, are obtained by using these entirely more soluble CD and βCD derivatives.

Details of the invention are illustrated in the following examples.

The drugs reported in the examples, belonging to different chemical and therapeutical classes, have been selected as test molecules as considered especially representatives of the invention. Particularly surprising results have been obtained with diphenylmethane, tricyclic and azole derivatives.

Nevertheless, it is evident that the present invention is applicable to every compound bearing basic groups.

EXAMPLE 1

Preparation of terfenadine-βCD-hydroxyacid soluble complexes 8 mmol of βCD, 4 mmol of terfenadine (TFN) and 5 mmol of tartaric acid (or 6 mmol of ascorbic acid or 4 mmol of lactic acid) were suspended in 60–70 ml of distilled water.

The suspensions were homogenized by vigorous stirring and ultrasonicated to obtain slightly opalescent solutions. After filtering the solutions across a glass prefilter, terfenadine content was determined by UV-photometry after 70 fold dilution with 50% aqueous ethanol. Concentrations of 27–29 mg/ml of dissolved terfenadine were detected.

Solid complexes were isolated from the clear solutions by freeze-drying.

The active ingredient content of the solid complexes was 15–17% (w/w) as measured by UV-photometry.

Powder X-ray analysis confirmed the formation of the complexes.

Solubility properties of the complexes.

100 mg of complexes prepared according to Example 1 were easily dissolved in 0.5 ml of distilled water resulting in clear solutions. After 30 fold dilution of the solution with 50% (v/v) ethanol, UV-photometry was used to determine the dissolved terfenadine concentration which resulted more than 30 mg TFN/ml.

Data relating to the complex obtained with tartaric acid are reported in Table 1 and those relating to the complex with citric acid in Table 2.

With a similar process, the terfenadine-βCD-glycerophosphoric acid complex (0.2/0.4/0.4 mmol) was prepared. The solubility of terfenadine with respect to said complex was 4 mg/ml.

EXAMPLE 2

Preparation of terfenadine-βCD-mono- or bicarboxylic acid complexes

Terfenadine (2 mmol) and βCD (4 mmol) were suspended into 25 ml of distilled water. 3 mmol of acetic acid (or 4 mmol formic acid) were added and the suspension was ultrasonicated for several minutes. The resulting slightly opalescent solutions, obtained by filtration, were freeze dried.

Active ingredient content of the complexes was determined by UV-photometry and gave 17±0.5%.

Redissolving properties of the complexes.

Redissolving properties of the complexes containing formic and acetic acid are also interesting: 100 mg of complex were easily dissolved in 0.5 ml of water resulting in a clear solution for the acetic acid and an opalescent solution for the formic acid-βCD complexes, respectively.

pH of these solutions resulted 4.36 for the complexes with acetic acid and 3.67 for the complexes with formic acid.

In a comparative test it was tried to dissolve 1 mmol of terfenadine into 15 ml of distilled water using 6 mmol of acetic or 4 mmol of formic acid.

The test was not successful and the highly hydrophobic terfenadine disappeared from the surface of the solution at the same time of the precipitation of the corresponding poorly soluble salt.

3.15 and 0.34 mg/ml of dissolved terfenadine were measured in the filtrate in the presence of acetic and formic acid, respectively.

With a similar process, the terfenadine-βCD-α-ketoglutaric acid complex (0.2/0.4/0.4 mmol, 1:2:2 ratio) was prepared. The solubility of terfenadine with respect to said complex was about 6 mg/ml.

EXAMPLE 3

Preparation of terfenadine-βCD-inorganic acid complexes

Terfenadine (1 mmol), βCD (2 mmol), 1 mmol of HCl (or 1 mmol of phosphoric acid) were suspended into 15 ml of distilled water. The suspension was ultrasonicated resulting in a slightly opalescent solution. Solid complexes were isolated by freeze-drying. Active ingredient content of the complex was 18±1%, as measured by UV-photometry.

Redissolving properties of the complexes.

100 mg of complexes were easily dissolved in 0.5 ml of distilled water or into HCl solution (pH 1.4) giving a clear solution. Terfenadine content of the solution was measured after 80 fold dilution with 50% (v/v) ethanol by UV-photometry. 29 mg/ml of dissolved terfenadine were measured. Addition of sodium chloride did not decrease the concentration of this highly saturated terfenadine-HCl-βCD solution.

EXAMPLE 4

Preparation of terfenadine-tartaric acid-γCD or βCD derivative complexes

Terfenadine (1 mmol), L(+) tartaric acid (1.5 mmol) and γCD (2 mmol) or 2 mmol of HPβCD; or 2 mmol of DIMEB or 2 mmol of RAMEB were suspended and ultrasonicated in 15 ml of distilled water.

The use of γ CD resulted in a slightly opalescent solutions, while the solutions obtained with HPβCD, DIMEB and RAMEB were clear. In addition, these latter CDs gave clear solutions even using 7.5 ml of distilled water only. The terfenadine content in these solutions was about 50 mg/ml.

EXAMPLE 5

Preparation of cinnarizine-βCD-hydroxyacid complexes

βCD (4 mmol), cinnarizine (2 mmol) and citric acid (3 mmol) (or tartaric acid (3 mmol)) were suspended into 20 ml of distilled water. The suspensions were homogenized and ultrasonicated to obtain slightly opalescent solutions. After filtering the solution across a glass prefilter, solid complexes were isolated by freeze-drying the solutions.

The active ingredient content of the complexes was found to be 11±0.5%, as measured by UV-photometry.

Redissolving properties of the complexes.

100 mg of complexes were dissolved in 0.5 ml of distilled water resulting in almost clear and slightly opalescent solutions in case of citric and tartaric acid complexes, respectively. pH of these highly supersaturated solutions was 2.5 and 2.3 for citric and tartaric acid complexes, respectively. After filtration across a 0.45 μm membrane filter, concentration of the solutions was measured after 2000 fold dilution with 50% ethanol by UV-photometry. 20–22 mg/ml of dissolved cinnarizine were measured. Calculated βCD concentration of the solutions was about 16–18% (p/v).

The data of the complex with tartaric acid are reported in Table 1.

EXAMPLE 6

Preparation of domperidone-βCD-tartaric acid complex 40 mmol of domperidone, 40 mmol of tartaric acid and 40 mmol of βCD were suspended into 700 ml of water and ultrasonically stirred till a slightly opalescent solution was obtained. After filtration through a sintered glass prefilter, solid complex was isolated by freeze drying.

The active ingredient content of the complex was found to be 27.4±0.1%, as measured by UV photometry.

Redissolving properties of the complexes.

100 mg of the complex were easily dissolved in 1 ml of distilled water. Domperidone content of this solution was 25 mg/ml.

Solubility date are reported in Table 1.

EXAMPLE 7

Preparation of domperidone-tartaric acid-HPβCD complex.

12 mmol of domperidone, 12 mmol of tartaric acid and 22 mmol of HPβCD (substitution degree=2.8) were suspended into 100 ml of distilled water and ultrasonically homogenized till a slightly opalescent solution was obtained. After filtration through a sintered glass prefilter, solid complex was isolated by freeze drying.

Active ingredient content: 14.0±0.2%, as measured photometrically.

Redissolving properties of the complex.

100 mg of complex were easily dissolved in 0.3 ml of distilled water. Domperidone content of this solution was 50 mg/ml.

Solubility data are reported in Table 3.

EXAMPLE 8

Preparation of other domperidone complexes

With a process similar to the one of the preceding examples, the following complexes were prepared:

8a) domperidone (4.4 mmol)-βCD (4.4 mmol)-lactic acid (1.1 mmol) (1:1:2.5 ratio);

8b) domperidone (4.4 mmol)-βCD (4.4 mmol)-malic acid (1.1 mmol) (1:1:2.5 ratio);

8c) domperidone (0.25 mmol)-βCD (0.5 mmol)-threonic acid (0.2 mmol) (1:2:2 ratio);

8d) domperidone (0.25 mmol)-HPβCD (0.5 mmol)-threonic acid (0.2 mmol) (1:2:2 ratio);

Spectrophotometric determination of domperidone in the four complexes gave 27.7%, 23.4%, 14.5% and 12.5%, respectively.

EXAMPLE 9

Preparation of astemizole complexes

With a process similar to the one of the preceding examples, the following complexes were prepared:

9a) astemizole (7.6 mmol)-βCD (6 mmol)-acetic acid (30 mmol).

UV Spectrophotometric determination of astemizole gave 33.9%.

9b) astemizole (7.6 mmol)-βCD (8 mmol)-malic acid (1.5 mmol).

UV Spectrophotometric determination of astemizole gave 25.6%.

9c) astemizole (7.6 mmol)-βCD (8 mmol)-L(+) tartaric acid (27 mmol).

UV Spectrophotometric determination of astemizole gave 22.5%.

Solubility characteristics of the complexes were determined in several systems: distilled water, phosphate buffer (pH 7.6), hydrochloric acid solution (pH 1.3).

Subsequent 0.1 ml portions of the dissolving medium were added to 200 mg of the complex, until a clear or slightly opalescent solution was obtained. After stirring and/or ultrasonication of the samples, astemizole concentrations were calculated in the solutions, whose pH was also measured.

Solubility data of the complex with tartaric acid are reported in Table 1.

EXAMPLE 10

Preparation of ketoconazole complexes

With a process similar to the one of the preceding examples, the following complexes were prepared:

10a) ketoconazole (1 mmol)-βCD (1.5 mmol)-tartaric acid (1 mmol);

10b) ketoconazole (1 mmol)-βCD (1.5 mmol)-citric acid (1 mmol);

Spectrophotometric determination of ketoconazole in the two complexes gave 21.6±0.5% and 21.7±0.5%, respectively.

Solubility data of the complex with tartaric acid are reported in Table 1.

EXAMPLE 11

Preparation of tamoxifene complexes

With a process similar to the one of the preceding examples, the following complexes were prepared:

11a) tamoxifene (1 mmol)-βCD (2 mmol)-tartaric acid (2 mmol), 11b) tamoxifene (1 mmol)-βCD (2 mmol)-citric acid (2 mmol);

11c) tamoxifene (1 mmol)-HPβCD (substitution degree 2.8, 2 mmol)-citric acid (2 mmol).

Tamoxifene content in the complexes resulted 12.2±0.1%; 12.3±0.1%; 11.5±0.1%, respectively.

Solubility data of the complex with βCD and citric acid are reported in Table 2.

EXAMPLE 12

Preparation of clomifene complexes

With the same process complexes with clomifene (2.5 mmol), βCD (2.5 mmol), and citric acid (7 mmol) or tartaric acid (5 mmol) were prepared.

Clomifene content resulted 17.9±0.1% and 18.2±0.1%, respectively.

Solubility data with citric acid are reported in Table 2.

EXAMPLE 13

Preparation of cyclobenzaprine (CBP)-βCD-tartaric acid complex 10 mmol of CBP.HCl were neutralized with 10 mmol NaOH and 10 mmol of βCD and 10 mmol of tartaric acid were suspended into 20 ml of water. The resulting clear, viscous solution was freeze dried.

The so obtained product contained 19.6% of CBP base (CBP.B), as determined by UV spectrophotometry.

500 mg of the complex were dissolved in 2.2 ml of water giving 45 mg/ml of CBP.B. After dissolving 100 mg of the above complex in 2, 4, 6, and 8 ml of buffer solution (pH=7.6) the following respective pH values were measured in the solutions: 4.85, 6.5, 7.0, and 7.25. The CBP content of these solutions was 10, 5, 3.3, and 2.5 mg/ml, respectively. No precipitation was observed at any dilution rate.

EXAMPLE 14

Preparation of itraconazole-βCD-hydrochloric acid complex 5 mmol of itraconazole, 10 mmol of βCD and 15 mmol of hydrochloric acid were ultrasonicated. The resulting very thick, homogeneous suspension was then diluted with 80 ml of distilled water and ultrasonication was continued for 20 min. The suspension was freeze dried.

The molar ratio of the complex was 1:2:3: with approximately 20% w/w itraconazole content.

The solubility of the complex in distilled water was appropriate. Equilibration of 100 mg of the complex in 2 ml of distilled water for 2–5 min resulted in more than 5 mg/ml of dissolved itraconazole, that means more than 20,000 fold solubility enhancement.

TABLE 1

Water solubility at room temperature of some basic, type drugs, their acid salts, their complexes with β-CD, their salts in β-CD solution and multicomponent complexes, expressed as drug concentration F (mg/ml).

| | FB | FB/AT | FB/βCD | FT/βCD | FB/AT/βCD |
|---|---|---|---|---|---|
| TERFENADINE | 0.010 [1x] | 0.340 [34x] | 0.080 [8x] | 3.3 [330x] | 50 [5000x] |
| ASTEMIZOLE | 0.004 [1x] | 3.270 [817.5x] | 0.065 [16x] | 7.9 [1975x] | 90 [22500x] |
| DOMPERIDONE | 0.005 [1x] | 10 [2000x] | 0.022 [4.4x] | | 25 [5000x] |
| KETOCONAZOLE | 0.050 [1x] | 21 [420x] | 1.24 [27x] | 21 [420x] | 110 [2200x] |
| CINNARIZINE | 0.1 [1x] | 9 [90x] | 0.5 [5x] | | 20 [2000x] |

FB   Basic-type drug
AT   Tartaric acid
βCD   β-Cyclodextrin
FT   Drug tartrate

TABLE 2

Water solubility at room temperature of some basic, type drugs, their acid salts, their complexes with β-CD, their salts in β-CD solution and multicomponent complexes, expressed as drug concentration F (mg/ml).

| | FB | FB/AC | FB/CD | FC/βCD | FB/AC/βCD |
|---|---|---|---|---|---|
| TAMOXIFENE | 0.03 [1x] | 0.3 [10x] | 0.06 [2x] | 11 [366x] | 20 [666x] |
| CLOMIFENE | 0.04 [1x] | 6.2 [155x] | 0.28 [7x] | 20 [500x] | 77 [1925x] |
| TERFENADINE | 0.01 [1x] | 0.76 [76x] | 0.08 [8x] | 4.2 [420x] | 50 [5000x] |

FB   Basic-type drug
AC   Citric acid
βCD   β-Cyclodextrin
FT   Drug citrate

TABLE 3

Water solubility of some basic type drugs, their complexes with a CD and multicomponent complexes, expressed as drug concentration F (mg/ml).

| DRUG | TERFENADINE | DOMPERIDONE | ASTEMIZOLE |
|---|---|---|---|
| FB | 0.01 | 0.005 | 0.004 |
| FB/α-CD | — | 0.033 (6.6x) | 0.024 (6x) |
| FB/AT/α-CD | — | 25 (5000x) | — |
| FB/γ-CD | — | 0.04 (8x) | 0.027 (6.6x) |
| FB/AT/γ-CD | 30 (3000x) | 30 (6000x) | — |
| FB/HPβ-CD | 1.23 (123x) | 0.16 (32x) | 0.353 (86x) |
| FB/AT/HPβ-CD | 60 (6000x) | 50 (10000x) | — |
| FB/DIMEB | 2.32 (232x) | 0.56 (112x) | 1.245 (303x) |
| FB/AT/DIMEB | 60 (6000x) | 30 (600x) | — |
| FB/RAMEB | 4.50 (450x) | 0.28 (56x) | 1.10 (275x) |
| FB/AT/RAMEB | 60 (6000x) | 30 (6000x) | |

FB   Basic-type drug
AT   Tartaric acid
α-CD   α-Cyclodextrin
γ-CD   γ-Cyclodextrin
HPβ-CD   Hydroxypropyl-β-Cyclodextrin
DIMEB   Dimethyl-β-cyclodextrin
RAMEB   RAndom MEthylated β-Cyclodextrin From the results reported in the above Tables 1, 2 and 3 the remarkable solubility enhancement obtained with the complexes of the present invention, may be observed.

This solubility enhancement is very important not only for the improvement of the biopharmaceutical characteristics of the compounds, but also for their bioavailability.

The presence in the complex of an excess amount of acid creates an acid environment which facilitates the dissolution of the drug also at high pH values, so that the dissolution characteristics of the compound are less dependent on the local pH.

Also in view of pharmaceutical technology, the advantages are remarkable. In fact, liquid pharmaceutical compositions, such as vials, drops, oral solutions, may be prepared also with hardly soluble drugs. Said compositions are a further object of the present invention.

As example, water amounts (ml) necessary to solubilize one unitary dose of terfenadine equal to 60 mg in different systems are reported.

| System | Water amount (ml) |
|---|---|
| Terfenadine | 6.000 |
| Terfenadine tartrate (79.2 mg) | 176 |
| Terfenadine-β-CD complex 1:2 (349 mg) | 750 |
| Terfenadine tartrate-β-CD complex 2:1 (380 mg) | 18 |
| Terfenadine-tartaric acid-β-CD complex (353–400 mg) | 1.2 |

Accordingly, the present invention provides the surprising use of β-CD as solubilizing agent in parenteral pharmaceutical compositions. Heretofore, said use has been hindered from the technological point of view by the low water solubility in comparison with the normal solutions volumes used in this kind of compositions.

EXAMPLE 15

Effect of some acids on the β-CD solubility

In a test tube 1000 mg of β-CD in 5 ml of a solution having different concentrations of an acid selected from tartaric, citric, lactic acid, were let to equilibrate for two days at 28*/−2° C. under stirring. The solution was filtered and β-CD concentration was determined by HPLC.

The results are reported in Table 4.

TABLE 4

| ACID | ACID CONCENTRATION (mg/ml) | β-CD CONCENTRATION (mg/ml) |
|---|---|---|
| Tartaric | 0 | 18.3 |
|  | 7.5 | 28.0 |
|  | 15.0 | 31.4 |
|  | 37.5 | 44.4 |
|  | 75.0 | 65.4 |
|  | 112.5 | 83.7 |
| citric | 0 | 18.3 |
|  | 9.6 | 34.1 |
|  | 19.2 | 47.9 |
|  | 48.0 | 86.1 |
|  | 96.0 | 140.1 |
|  | 144.0 | 195.7 |
| lactic | 0 | 18.3 |
|  | 4.5 | 17.1 |
|  | 9.0 | 18.8 |
|  | 22.5 | 24.2 |
|  | 45.0 | 31.0 |
|  | 67.5 | 35.8 |

Hydroxyacids (tartaric and citric acid) remarkably enhance the water solubility of β-CD, depending on their concentration.

Lactic acid instead exerts a lower effect even if it is effective in the formation of multicomponent complexes, as shown in the examples.

In fact, the surprising enhancement of the β-CD solubility in the multicomponent complexes should not exclusively be attributed to the effect of the acid.

In the multicomponent complexes of terfenadine and tartaric or citric acid, for example, the concentration of β-CD is about 150 mg/ml, about 8 times higher than water solubility of β-CD as such.

In the binary system acid-β-CD, in the presence of the same acid concentrations, namely 11 and 17 mg/ml respectively, the increase of the β-CD solubility is about 2 times.

Some cyclodextrins may be used not only as complexing agents, but also as solubilizing agents in the preparation of liquid pharmaceutical compositions. Among these, the most used one appears to be HPβ-CD.

Also in this case the technological advantages, which are connected with the use of the complexes according to the present invention, appears evident. Accordingly, not only higher drug concentrations in solution are obtained, but also with the same amount of dissolved drug, the amount of cyclodextrin is considerably reduced.

Table 5 shows the amounts of HPβ-CD necessary for the solubilization of the same amount of drug depending on the use of cyclodextrin in a multicomponent complex or as conventional solubilizing agent.

TABLE 5

HPβ-CD amount (mg), in the form of multicomponent complex or of conventional solubilizing agent, necessary to solubilize 10 mg of Terfenadine or Domperidone or 100 mg of Ketoconazole, respectively. The drug content in the complex or the drug concentration in the solution are reported within brackets.

|  | Drug amount (F) (mg) | HPβ-CD content (mg) |
|---|---|---|
| Terfenadine-HPβ-CD-tartaric acid multicomponent complex (F = 14%) | 10 | 57.3 |
| Terfenadine-10% HPβ-CD solution (F = 1.23 mg/ml) | 10 | 803 |
| Domperidone-HPβ-CD-tartaric acid multicomponent complex (F = 14%) | 10 | 57.3 |
| Domperidone-1% HPβ-CD solution (F = 0.16 mg/ml) | 10 | 6240 |
| Ketoconazole-HPβ-CD-tartaric acid multicomponent complex (F = 20%) | 100 | 375 |
| Ketoconazole-HPβ-CD solution* (F = 25 mg/ml in 60% HPβ-CD) | 100 | 2400 |

*solution added with 10% propylene glycol and HCl to pH 2.1.
F = Drug

The remarkable decrease of the HPβCD amount, necessary to the drug solubilization using the complexes of the present invention, is advantageous also from a toxicological point of view, particularly for parenteral formulations.

Finally, the semplicity of the technology of preparation of the complexes of the present invention, which represents a further advantage for the industrial applicability, is to be underlined.

We claim:

1. A multicomponent inclusion complex, comprising a basic drug, an acid and a cyclodextrin, obtained by combining said basic drug in unsalified form, said acid and said cyclodextrin.

2. The complex of claim 1, wherein said acid is an aliphatic carboxylic acid.

3. The complex of claim 2, wherein said aliphatic carboxylic acid has one or more oxygen-containing substituents thereon.

4. The complex of claim 3, wherein said oxygen-containing substituents are keto or hydroxy groups.

5. The complex of claim 1, wherein said acid is selected from the group consisting of hydrochloric acid, hydrobromic acid, acetic acid, propionic acid, butyric acid, oxalic acid, succinic acid, glutaric acid, pimelic acid, tartaric acid, malic acid, citric acid, maleic acid, malonic acid, α-ketoglutaric acid and threonic acid.

6. The complex of claim 5, wherein said acid is selected from the group consisting of citric acid, tartaric acid, α-ketoglutaric acid and threonic-acid.

7. The complex of claim 5, wherein said acid is hydrochloric acid.

8. The complex of claim 1, wherein said cyclodextrin is selected from the group consisting of α-cyclodextrin, β-cyclodextrin, γ-cyclodextrin, hydroxypropyl-β- cyclodextrin, dimethyl-β-cyclodextrin and random methylated β-cyclodextrin.

9. The complex of claim 1, wherein said basic drug is a diphenyl methane, tricyclic or azole compound.

10. The complex of claim 1, wherein said basic drug is selected from the group consisting of terfenadine, astemizole, domperidone, ketoconazole, cinnarizine, tamoxifene, clomifene, cyclobenzaprine and itraconazole.

11. A method for preparing a multicomponent inclusion complex, comprising the steps of:
   (a) suspending a basic drug in unsalified form, an acid and a cyclodextrin in water to form a suspension;
   (b) homogenizing said suspension to obtain a clear or opalescent solution;
   (c) optionally filtering said solution to obtain a clear solution; and
   (d) dehydrating the resulting solution.

12. The method of claim 11, wherein said water is distilled water.

13. The method of claim 11, wherein said homogenizing is performed by stirring, sonication or a combination thereof.

14. A pharmaceutical composition, comprising the multicomponent inclusion complex of claim 1 and a pharmaceutically acceptable carrier.

15. A method of increasing the water-solubility of acyclodextrin, comprising mixing an acid selected from the group consisting of organic acids and halogenhydric acids, with said cyclodextrin.

16. The complex of claim 1, wherein said acid is an organic acid.

17. The method of claim 11, wherein said acid is an organic acid.

18. The method of claim 15, wherein said acid is an organic acid.

19. The method of claim 15, wherein the acid is an organic acid.

\* \* \* \* \*

UNITED STATES PATENT AND TRADEMARK OFFICE
CERTIFICATE OF CORRECTION

PATENT NO. : 5,855,916
DATED      : January 5, 1999
INVENTOR(S): Paolo CHIESI et al.

It is certified that error appears in the above-identified patent and that said Letters Patent is hereby corrected as shown below:

On the title page, item [21] Application No. should be:

--[21] Appl. No.:   481,519--

Signed and Sealed this

First Day of June, 1999

Attest:

Q. TODD DICKINSON

*Attesting Officer*    *Acting Commissioner of Patents and Trademarks*